United States Patent [19]

Arenas et al.

[11] Patent Number: 5,242,430
[45] Date of Patent: Sep. 7, 1993

[54] LIMITED TURN HANDLE FOR CATHETER
[75] Inventors: Alvaro E. Arenas; Paul J. Costigan, bot of Miami, Fla.
[73] Assignee: Cordis Corporation, Miami, Fla.
[21] Appl. No.: 642,388
[22] Filed: Jan. 17, 1991
[51] Int. Cl.⁵ .............................................. A61M 29/02
[52] U.S. Cl. .................................... 604/280; 604/154
[58] Field of Search ............................... 604/96–101, 604/280, 95, 283; 606/191–195

[56] References Cited
U.S. PATENT DOCUMENTS
4,664,113 5/1987 Frisbie et al. ..................... 606/194

Primary Examiner—C. Fred Rosenbaum
Assistant Examiner—William Lewis
Attorney, Agent, or Firm—Gerstman & Ellis, Ltd.

[57] ABSTRACT

A rotary handle for attachment to a proximal end of a catheter. The handle comprises a handle member, and a tubular grip member rotatably affixed in generally coaxial relation about a portion of the handle member. An apertured, elastomeric block is provided to permit connection to the proximal end of a catheter. The handle member and grip member are relatively rotatable, to provide corresponding rotation of a connected catheter, typically through a predetermined rotation range, while preventing further catheter rotation to prevent its over rotation while emplaced in a patient. Preferably, the catheter defines a proximal, rigid, tubular tip that passes through the elastomeric block. Also, the catheter may have a steering wire having a zig-zag proximal end positioned within the rigid, tubular tip under compression so that the zig-zag end is frictionally retained within the tubular tip to cause the steering wire to rotate the catheter.

22 Claims, 3 Drawing Sheets

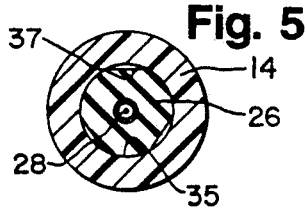
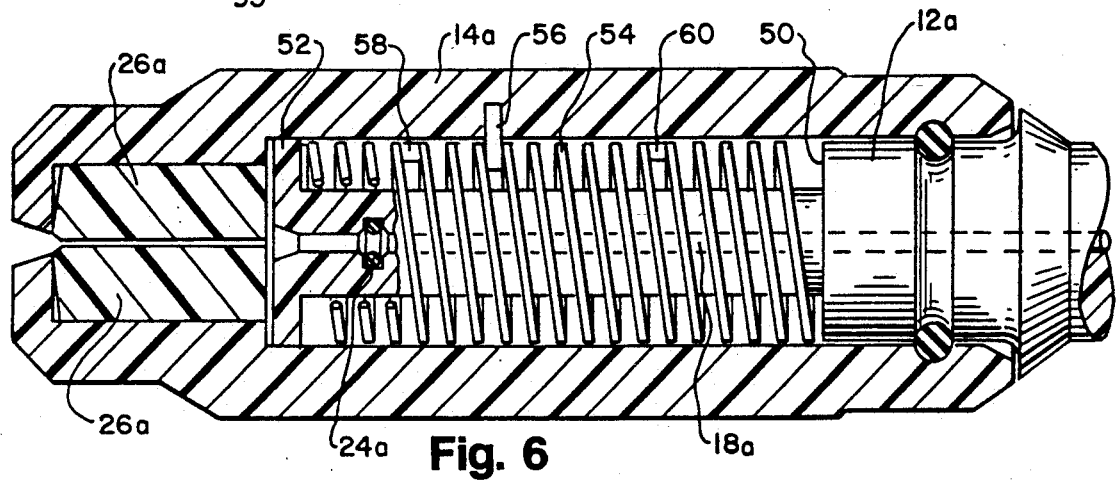
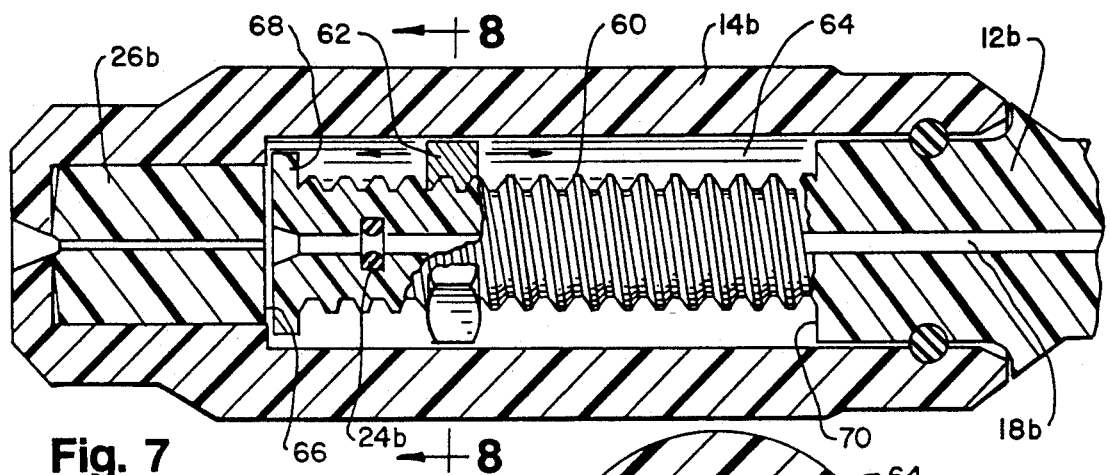
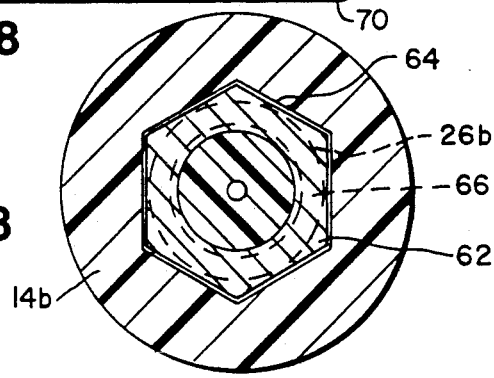

LIMITED TURN HANDLE FOR CATHETER

BACKGROUND OF THE INVENTION

Steering catheters are catheters which are capable of passing through the arteriovenous system of a patient, typically to bring the distal tip of the catheter to a site of a stenotic lesion which threatens to occlude an artery, or to the heart itself for diagnosis, treatment, and the like. The catheter is "steerable" by rotation, typically having a curved tip, so that the catheter can be advanced along a desired pathway through the network of blood vessels. Such steerable catheters may carry a central steering wire which is attached to the catheter at both the proximal and distal ends, to provide to the catheter a torsional stiffness so that when the proximal end is rotated, the distal end of the catheter is correspondingly rotated. Additionally or alternatively, the catheter may carry a braided sheath within its tubular wall to provide added rotational stiffness as well as "pushability", which is a measure of longitudinal stiffness, without causing the catheter to be unduly laterally stiff so it cannot advance through the blood vessel system to its desired location.

Typically, in the prior art the surgeon who is performing a medical procedure with a steerable catheter advances the catheter while rotating a portion of the catheter outside of the body with his thumb and forefinger, all the while observing the progress of the catheter through a fluoroscope. This can be a difficult and inconvenient procedure because the catheter is typically very small in diameter so as to permit its entrance into smaller arteries and blood vessels. Thus, the catheter is hard to grip with the thumb and forefinger, and is also hard to rotate.

By this invention, a handle is provided to the catheter which is much more easily gripped by the surgeon, being typically of larger diameter than the catheter, and having a stationary portion for holding in the hand, plus a rotatable portion for rotational steering of the catheter. Also by this invention, the rotary handle is typically limited in the amount of rotation that it can perform, to consequently limit the overall rotation of the catheter to a given number of turns. This is advantageous in that it prevent excessive torque from being delivered to the catheter.

Additionally, it is possible to connect the catheter through the rotary handle of this invention to a source of fluid pressure for inflation of the catheter balloon when such a balloon is present, while at the same time rotating the catheter as desired by means of the rotary handle. The rotary handle may be held and manipulated with only one hand, but with substantially greater ease than a surgeon holds and manipulates the catheter per se. Furthermore, the handle of this invention may be connected to a catheter simply by inserting the proximal end of the catheter into the handle, with the handle providing sufficient gripping force to hold the catheter in use.

DESCRIPTION OF THE INVENTION

In this invention, a rotary handle is provided for attachment to the proximal end of a catheter. The rotary handle comprises a handle member, and a tubular grip member which is rotatably affixed in generally coaxial relation about a portion of the handle member. Means are carried by one of the handle member and the grip member for connection to the proximal end of a catheter. The handle member and grip member together define means permitting their relative rotation, and corresponding rotation of a connected catheter, typically through a predetermined rotational range while preventing further relative rotation and catheter rotation. This prevents over rotation of a catheter connected thereto while emplaced in a patient, while at the same time providing an improved and easier way for the surgeon to rotate the catheter.

As specifically shown in the drawings, the tubular grip member carries the means for connection to the proximal end of the catheter, so that the tubular grip member can be rotated with the fingers while the surgeon grasps the remainder of the handle, for ease of catheter rotation with one hand.

Typically, either the tubular grip member or the handle member portion carries a helical slide member facing the other of the grip member and handle member portion. This slide member may be screw threads facing outwardly from the handle member portion or inwardly from the tubular grip member.

Then, a second slide member is provided, which second slide member is rotatable with the other of the grip member and handle member portion which does not carry the helical slide member. This second slide member is positioned to rotationally slide between the coils of the helical slide member as the grip member and the handle member relatively rotate. Means are also provided, associated with the helical slide member, for limiting the range of the rotational sliding of the second slide member. Thus, when the second slide member comes to the end of its range of rotational sliding, the tubular grip member and handle member portion can no longer further rotate in that direction, so that the rotational range between the two members can be limited, in both directions of rotation if desired.

Preferably, the handle member defines a longitudinal bore, plus means for connecting the bore at one end thereof to a catheter proximal end. It should be noted that this connection may be in addition to the connection means between the tubular grip member and the catheter proximal end. Either one of these connection means may be used to cause the catheter to rotate with either one of the members. Additionally, connector hub means are provided, communicating with the bore of the handle member at its other end, to provide fluid communication through the handle member to the catheter. Specifically, pressurized fluid may be provided this way so that a catheter balloon is inflatable and deflatable while the catheter is connected to the handle of this invention.

When the helical slide member defines a thread, the second slide member may comprise a projecting member such as a ball bearing slidable in a longitudinal slot defined by the other of the grip member and handle member which do not define the helical slide member thread.

Alternatively, the second slide member may comprise a nut rotatably mounted about the helical slide member thread described above, with the nut having external or internal threads depending upon whether the grip member or handle member define the helical slide member thread. The nut is mounted to engage and to slide along a non-circular slide track of the other grip member and handle member which does not carry the helical slide member, to permit the nut to slide longitudinally, while preventing relative rotation between the nut and such other member.

As a further alternative, the rotary slide member may define a coil spring, being attached to either the tubular grip member or the handle member. In that circumstance, the other of the tubular grip member or the handle member defines a projection which extends between the coils of the coil spring. Then, to limit the range of rotation of the system, one or more obstructions can be secured between respective coils of the coil spring, which prevent the projection and the coil spring to relatively rotate beyond the obstruction, for limitation of the rotational range of the handle of this invention by another means.

Preferably, the tubular grip member defines a bore that contains one end of the handle member. The bore also contains, distal to the handle member, an elastomeric retention block having a longitudinal passageway for receiving a catheter proximal end. The passageway normally, in the unstressed condition of the elastomeric retention block, is of less diameter than the catheter end received therein. Thus, the catheter is frictionally retained, to be rotatable with the tubular grip member.

Typically, the proximal end of the catheter defines a rigid, tubular tip. The catheter typically extends completely through the elastomeric retention block described above, with the handle member portion defining a longitudinal bore for receiving the rigid, tubular tip of the catheter. The longitudinal bore extends through O-ring means carried in the handle member, so that the rigid, tubular tip extends through and engages the O-ring means in sealing relation. Thus, the bore extending through the handle member portion may communicate with the bore of the catheter in sealed manner, even in that circumstance where the catheter rotates with the tubular grip member, which causes the rigid, tubular catheter tip to rotate in the O-ring without loss of sealing.

Also, a catheter is disclosed in this invention which defines a proximal, rigid, tubular tip which is typically made of a metal such as stainless steel. The catheter defines a steering wire extending from the tip to a connection site at a distal catheter location. The steering wire has a zig-zag proximal end positioned within the rigid, tubular tip. The zig-zag end of the steering wire has a transverse dimension, in its natural, unstressed shape, that is larger than the inner diameter of the rigid, tubular tip. Accordingly, the zig-zag end is frictionally retained in the tubular tip by the pressure imparted to it by being stretched out of its normal configuration, so that the steering wire rotates with the catheter.

Thus, by this invention, a rotary handle and a catheter for attachment with the rotary handle is provided. The catheter is typically of the steering catheter type, and the rotary handle of this invention permits the surgeon to rotate the catheter in the steering operation with greater ease than when the surgeon attempts to rotate the catheter by itself. The handle of this invention can be held in the palm of the hand, and may be connected to a source of fluid to provide a continuous pressure as desired to the lumen of the catheter through the handle without leakage, while the catheter may be continuously rotated in any manner desired. Additionally, the catheter is not easily pushed out of the handle during pressurization. The catheter may be easily loaded onto the handle by a simple pushing-in action. Likewise the handle of this invention has major components that "snap fit" together for ease of assembly.

DESCRIPTION OF THE DRAWINGS

In the drawings.

FIG. 5 is a sectional view taken along line 5—5 of FIG. 1;

FIG. 6 is a longitudinal sectional view of a modified embodiment of limited turn handle which is otherwise similar to the embodiment of FIG. 1;

FIG. 7 is a longitudinal section view of yet another embodiment of limited turn handle which is otherwise similar to the embodiment of FIG. 1;

FIG. 8 is a sectional view taken along line 8—8 of FIG. 7;

DESCRIPTION OF SPECIFIC EMBODIMENTS

Figure 1:
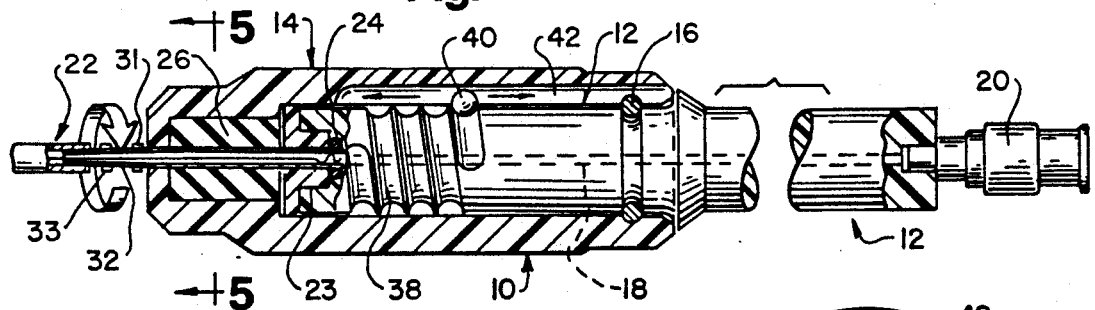
FIG. 1 is a side view, taken partly in section, of one embodiment of the limited turn handle of this invention, carrying a catheter engaged in accordance with this invention.

Referring to FIGS. 1-5, the rotary handle 10 of this invention is shown, comprising a handle member 12, and a tubular grip member 14 which is rotatably affixed in generally coaxial relation about a portion of handle member 12, particularly its distal end. Any desired mode of affixing members 12 and 14 together in rotatable relation can be used, but, in the specific embodiment shown, a polytetrafluoroethylene snap ring 16 fits into respective annular grooves of handle member 12 and grip member 14, to prevent their relative longitudinal motion while permitting rotary motion. Also, grip member 14 may be made of two semi-cylindrical halves which are bonded together in place at their edges.

Handle member 12 may be of any desired size, and is particularly sized to fit in the hand. As shown, handle member 12 defines a bore 18 extending longitudinally therethrough. At the proximal end of bore 18 there is provided a connector hub 20 of conventional design so that bore 18 may be brought into fluid connection with a source of pressurized fluid, typically for inflating a catheter balloon. At the distal end of handle member 12 there is provided a system for connection with a catheter 22, which may typically be an angioplasty balloon catheter, typically having modifications as described herein, but otherwise being conventional. Specifically, catheter 22 may have a rigid, tubular, proximal end piece 32 proportioned for insertion into rotary handle 10.

The distal end of handle member 12 carries a hard plastic end cap 23, typically made of polytetrafluoroethylene (PTFE), having an extension 19 of bore 18, and enclosing in a sightly enlarged chamber for an elastomeric O-ring 24, which may be made of silicone rubber or the like.

Tubular grip member 14 may carry in an inner recess, distal to the end of handle member 12, an elastomeric block 26 of silicone rubber or the like, defining a longitudinal bore 28 which is preferably of less diameter than the outer diameter of catheter 22 to which the handle member 10 is to be attached, so that the attachment at silicone block 26 can be a strong, compressive, frictional attachment. Such attachment which is sufficient to rotationally affix the catheter to grip member 14, without being so great as to collapse the catheter lumen so that flow cannot take place therethrough, in circumstances where the catheter proximal end is flexible. For example, the diameter of bore 28 may be about 0.012 inch, while the outer diameter of catheter 20 may be, for example, 0.032 inch. The preferably soft elastomer of block 26 is stretched outwardly by the presence of catheter 22, to provide high friction gripping of the catheter by grip member 14.

Figure 3:
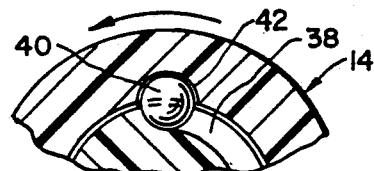
FIG. 3 is a sectional view taken along line 3—3 of FIG. 2.
Figure 4:
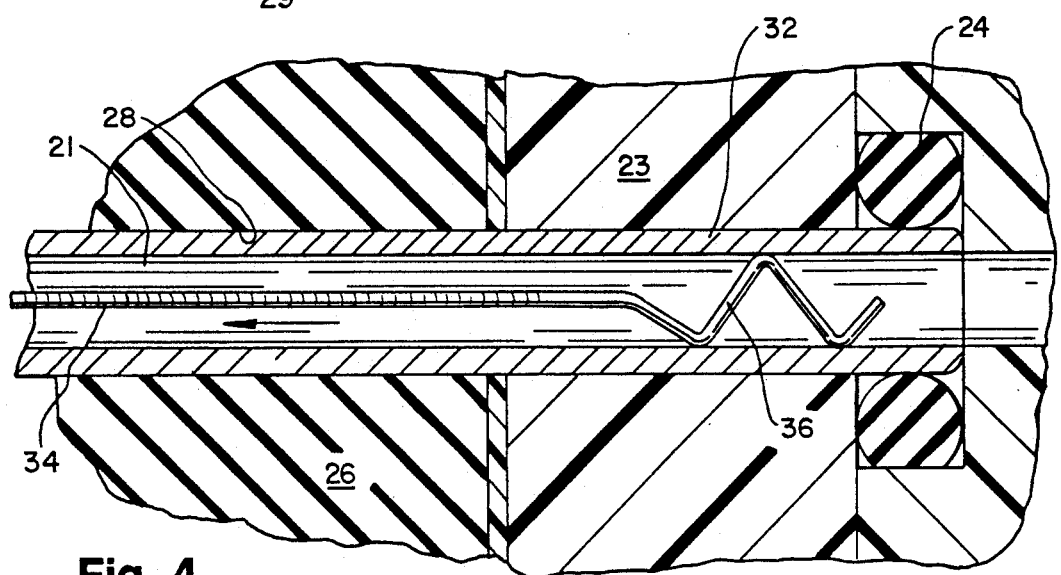
FIG. 4 is a greatly enlarged, longitudinal sectional view of a portion of FIG. 2, with a catheter proximal end installed.

At the same time, as shown in the enlarged FIGS. 3 and 4, the proximal end of a catheter 22 may be inserted into the distal end aperture 30 of rotary handle 10. Catheter 22 is pressed completely through bore 28 of silicone rubber block 26 and optional PTFE washer 29, to penetrate inwardly through bore 19 of plastic member 23. In currently preferred embodiments, catheter 22 defines a rigid, tubular tip 32 at its proximal end, typically made of a metal such as stainless steel. Tip 32 can enter into engagement with O-ring 24. Thus, the user can hold handle member 12 in his hand, and can rotate tubular grip member 14 with his fingers, with a catheter 22 installed in the rotary handle 10 as shown. Because of the strong gripping action of elastomeric block 26 on the catheter, it rotates with the rotation of tubular grip member 14. This, in turn, causes rotation of rigid, tubular tip 32 in plastic end cap 23 secured to handle 12 and O-ring 24, where less frictional retention is brought to bear than in the are of elastomeric block 26. Alternatively, end cap 23 may be secured at its periphery 25 to grip member 14 to rotate therewith relative to handle 12.

Thus, as grip member 14 rotates with respect to handle member 12, elastomeric block 26, carried in the grip member, rotates with respect to O-ring 24, with catheter 22 and rigid proximal tip 32 correspondingly rotating with elastomeric block 26. Since rigid tip 32 is seated in O-ring 24, this rotation can take place without fluid leakage. Thus, as the catheter is being used and manipulated, even with rotational action provided by the rotation of grip member 14, fluids such as catheter balloon inflation fluid can be inserted and withdrawn through hub 20 and bore 18 into and out of catheter 22 without significant leakage.

Particularly when end cap 23 rotates with handle 14, a vent passage 27 may be provided between handle 12 and end cap 23. Thus if the sealing of O-ring 24 should fail, high fluid pressures can be vented between members 12 and 14 to avoid popping apart of the two members.

As illustrated, catheter 22 is a steerable-type catheter having a central steering wire 34, of generally conventional design. As a modification in accordance with this invention, steering wire 34 may define a proximal end 36 of zig-zag shape in which the zig-zag end 36 has a transverse dimension in its natural, unstressed shape that is larger than the inner diameter of rigid, tubular tip 32. Thus, since zig-zag end 36 is forced into a stretched-out configuration, it exerts laterally outward force against rigid tip 32, and thus is frictionally retained in the tubular tip with a force sufficient to provide the desired torsional stiffness to the entire catheter. This is done without the need for welding or adhesives, but rather provides merely a desired frictional bond, which simplifies the manufacture of the catheter, and also provides a maximum torsional stiffness at which the zig-zag portion 36 ca start slipping torsionally. This later advantage is significant in that it can prevent excessive torsional force from being applied to body tissues through the catheter.

Silicone rubber block 26 may reside in a bore of handle member 14 which is of cylindrical cross section, as shown in FIG. 5. However, it is preferable for elastomeric block 26 to be of non-cylindrical outer cross section, having a plurality of flat surfaces 37 defined on its periphery. These surfaces 37 interacting with the cylindrical cross section of the bore 35 define several spaces as shown. These spaces, in turn, provide a broader tolerance for the diameter of catheter proximal end 32 which may be inserted into bore 28 of elastomeric block 26, so that a given handle member 10 may be used with a larger size range of the catheters.

Also, rigid, tubular tip 32 may define a pair of raised rings or other indicia 31, 33 (FIG. 1). The distal raised ring 31 may be positioned so that when catheter tip 32 is passed into handle member 10, the arrival of ring 31 to the distal end of member 14 indicates that the catheter has been moved in far enough for proper securance with O-ring 24. Then, ring 33 may be provided so that the user can obtain a grip with the finger nails upon it, to facilitate the pulling of catheter end 32 out of handle member 10 when that is desired.

A distal portion of handle member 12 defines a helical groove 38, corresponding to the helical slide member previously described. Ball 40, previously described as the second slide member, slides or rolls in the helical groove 38.

Additionally, tubular grip member 14 defines a longitudinal groove 42 in which ball 40 also slides or rolls, so that ball 40, which may typically be made of stainless steel or hard plastic, is constrained within the two groove systems 38, 42 which intersect each other as shown.

Thus, as the user rotates handle member 14, ball 40 slides or rolls along helical groove 38 of handle member 12, which naturally forces ball 40 to move along longitudinal groove 42. In FIG. 1, ball 40 is shown to be near one end of helical groove 38. Upon a further clockwise rotation of grip member 1 in the direction shown by the arrow of FIG. 1, ball 40 will come to one end of helical groove 38, at which point it will no longer be possible to rotate grip member 14 in that direction.

Figure 2:
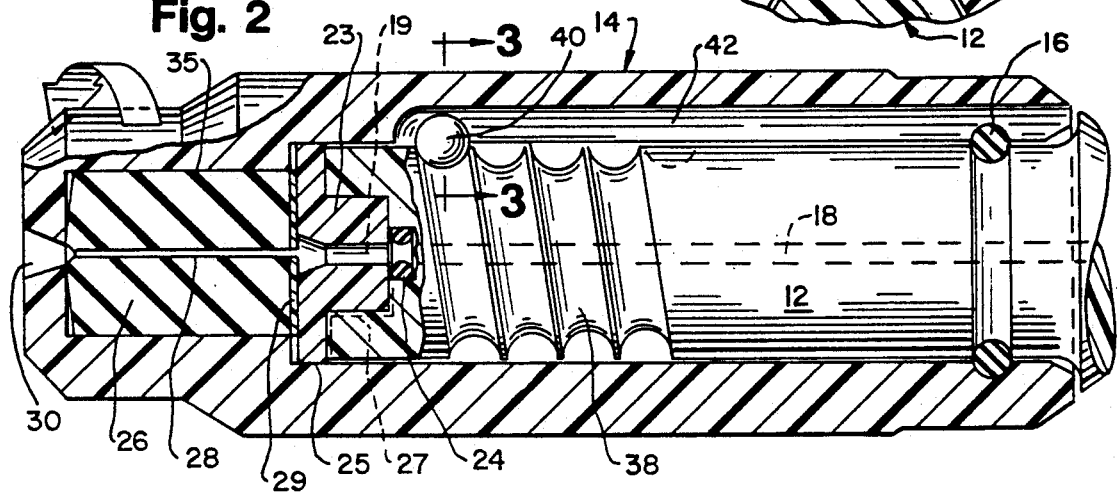
FIG. 2 is an enlarged, longitudinal sectional view of a portion of the handle of FIG. 1.

Similarly, as shown in FIGS. 2 and 3, when grip member 14 is rotated in the opposite direction illustrated by the arrow of FIG. 2, it eventually comes to the other end of helical groove 38, to limit that direction of rotation as well.

Thus, the rotary handle of this invention may be adapted by appropriate selection of the length of helical groove 38, or if desired, by selection of the length of longitudinal groove 42, to limit the range of rotation of the rotary handle of this invention. This has important clinical advantages in that this can prevent excessive torque from being delivered to the catheter while emplaced in the patient. At the same time, fluids can be delivered as desired without regard to the rotational position of the catheter, or whether or not the catheter is being rotated, and the ease of rotation is greatly facilitated for the surgeon.

As an alternative embodiment, it would be possible to put the helical groove 38 on an inwardly facing surface of grip member 14, while the longitudinal groove is placed on an outwardly facing surface of handle member 12. A ball member or other sliding member analogous to ball 40 could then reside at an intersection of the two grooves as in this present embodiment for equivalent functioning.

Additionally, if desired, the catheter connection site could be placed upon the exposed end of handle member 12, so that one would grip the outer, tubular grip member 14 and rotate the handle member 12, to rotate the catheter in a manner equivalent to the specific embodiment shown and capable of possessing the same advantages.

A washer member 29 may be attached on the proximal end of elastomeric block 26 to provide a rotational bearing surface against PTFE end cap 23.

Referring to FIG. 6, another modification of the rotary handle of this invention is disclosed, with portions not shown being similar to the rotary handle in FIG. 1.

As before, a handle member 12a carries at one end thereof a tubular grip member 14a. Handle member 12a and tubular grip member 14a carry a system for receiving and gripping a catheter which is essentially the same as in the previous embodiment, with elastomeric block 26a being carried by the tubular grip member 14a and aperture with O-ring 24a being carried by handle 12a for sealing the connection between bore 18a and the catheter.

By this invention, handle member 12a defines a pair of annular abutment members 50, 52 which carry and retain a coil spring 54. Spring 54 is typically affixed at its ends to the respective abutment members 50, 52. Grip member 14a defines an inwardly extending, fixed projection 56 which extends between the coils of spring 54. Thus, when a catheter is installed into the handle member of FIG. 6, and grip member 14a is rotated to rotate the catheter frictionally retained in the elastomeric block 26a, the coils of coil spring 54 travel past projection 56, with the coils being forced to one side or the other of projection 56. Stop members 58, 60 are attached between adjacent coils of spring 54 and are respectively positioned on each side of projection 56.

Thus, when the rotation of grip member 14a proceeds in one direction far enough, the respective coils of spring 54 are distorted to bring projection 56 and stop member 58 together, at which point it no longer is possible to rotate grip member 14a in that direction any farther.

Correspondingly, when grip member 14a is rotated in the other direction, projection member 56 rotates through the coiled path between the coils of spring 54, distorting spring 54, until it encounters stop member 60. At this point also, it becomes impossible for grip member 14a to rotate any further.

Thus, the rotary handle of FIG. 6 is provided with the desired rotation limitation discussed above.

Stop members 58, 60 may be glued or welded into their position between the various coils of spring 54.

Turning to FIGS. 7 and 8, another embodiment of the rotary handle of this invention is disclosed. As before, except as otherwise described, this embodiment has a structure and function similar to the embodiment of FIGS. 1 through 5.

As before, handle member 12b carries grip member 14b in rotational manner about an end thereof, with the two members being attached in a manner similar to previous embodiments. The means for attaching a catheter to the handle member is also essentially the same, with elastomeric block 26b being carried by grip member 14b, for sealed fluid connection with bore 18b of handle member 12b, assured by the presence of O-ring 24b.

In this embodiment, the distal end of handle member 12b is threaded with what may be a standard dimension screw thread 60, being analogous in function to helical channel 38 of the FIG. 1 embodiment.

A nut 62, which is shown to be of hexagonal shape, but may be of any desired non-circular shape, is mounted on helical thread 60 for rotary action in the conventional manner of a nut on a bolt. However, as shown particularly in FIG. 8, nut 62 fits in a non-circular bore 64 of grip member 14b, which is specifically shown to be hexagonal to fit nut 62 and thus to prevent rotation. The close fitting of bore 64 and the outer periphery of nut 62 in not mandatory, as long as the interrelationship prevents relative rotation of the nut with grip member 14b.

It can be seen that the face 66 of elastomeric plug 26b may be circular in cross section if desired.

Accordingly, after installation of a catheter through elastomeric plug 26b into engagement with O-rings 24b, a sealed flow path through the catheter and rotary handle is provided, and grip member 14b may be rotated relative to handle member 12b to rotate the catheter as may be desired, for a procedure in which the catheter is inserted into the patient with "steering" as the catheter is advanced. As grip member 14b is rotated on handle member 12b, nut 62 moves longitudinally back and forth as indicated in the arrows of FIG. 7. Thus, the range of rotation of grip member 14b is limited to that range in which nut member 62 can move longitudinally. When nut member 62 comes into engagement with either of abutment between grip member 14b and handle member 12b must terminate, to provide the desired limitation of the catheter rotation to prevent the application of excessive torque on the catheter.

The respective handle members and grip members disclosed herein may be made of a polycarbonate plastic, as may proximal hub 20.

Figure 9:
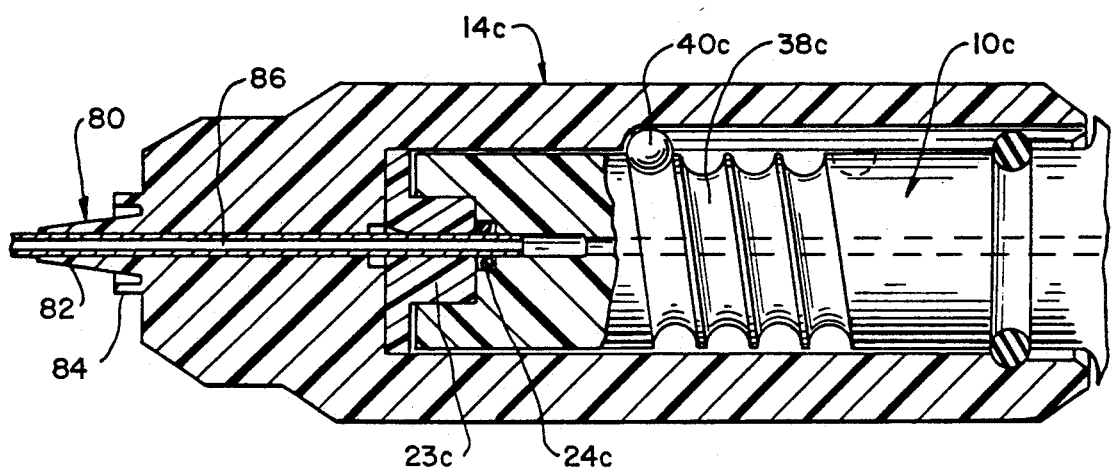
FIG. 9 is a longitudinal sectional view of another handle embodiment.

Referring to FIG. 9, at another embodiment of a handle 10c is shown. As before, handle member 12c carries a grip member 14c in rotating relation thereto. Except as otherwise described, this embodiment also functions in a manner similar to the previous embodiments. However, in this situation, the prior elastomeric retention block may be eliminated, with the retention of the catheter being provided by a luer lock connector 80 which comprises a conventional male luer taper 82 and a typically threaded sleeve 84, with both members 82 and 84 mating with corresponding members on the proximal end of a catheter, to releasably lock the catheter in position on the handle. Bore 86 containing a catheter end, then leads from the luer lock connector 80 through the distal portion of grip member 14c to a bore in end cap 23c, which end cap is similar to previous designs. O-ring 24c is also provided for sealing purposes. Handle member 14c and end cap 23c can be sealingly attached, so that the rotation between grip member 14c and handle member 12c may be sealed at the rotational sliding area between end cap 23c and handle member 12c.

The threaded arrangement 38c in handle 12c and the ball member 40c may operate in a manner similar to the embodiment of FIGS. 1-5.

Thus, this handle structure 10c is simplified, and is effective for use with catheters that have a luer connector on their proximal ends.

Figure 10:
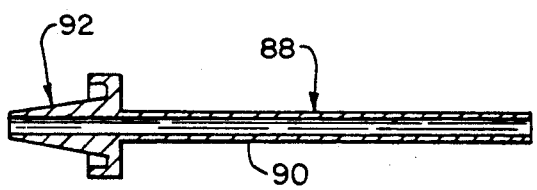
FIG. 10 is a longitudinal sectional view of an adaptor member for adapting catheters to receive the handle of this invention.

Referring to FIG. 10, an adaptor 88 is provided to permit a catheter having a luer connector on its proximal end to be adapted for use with handle members of the types shown in FIGS. 1-8. Adaptor 88 may comprise a rigid, typically stainless steel tube 90, which carries a luer lock connector 92 similar to the design of connector 80. Thus, connector 92 may be connected to the luer connector of a catheter to provide to that catheter a rigid tube 90 in sealed relation, which then can be used to penetrate a rotary handle of this invention in a manner similar to the rigid proximal end catheter end 32 previously described.

The above has been offered for illustrative purposes only, and is not intended to limit the scope of the invention of this application, which is as defined in the claims below.

That which is claimed is:

1. A rotary handle for attachment to the proximal end of a catheter, which comprises: a handle member; a tubular grip member rotatably affixed in generally coaxial relation about a portion of said handle member; means carried by one of said handle member and grip member for connection to the proximal end of a catheter; said handle member and grip member together defining means permitting their relative rotation, and corresponding rotation of a connected catheter, through a predetermined rotational range but preventing further relative rotation and catheter rotation, to prevent over rotation of a catheter connected thereto while emplaced in a patient.

2. The rotary handle of claim 1 in which one of said tubular grip member and handle member portion carries a helical slide member facing the other of said grip member and handle member portion, a second slide member, rotatable with the other of said grip member and handle member portion, said second slide member being positioned to rotationally slide between coils of said helical slide member as the grip member and handle member portion relatively rotate, and means, associated with said helical slide member, for limiting the range of said rotational sliding of said second slide member.

3. The rotary handle of claim 2 in which said handle member defines a longitudinal bore, plus means for connecting said bore at one end thereof to a catheter proximal end, and connecter hub means communicating with said bore at the other end thereof.

4. The rotary handle of claim 2 in which said helical slide member defines a thread and groove system.

5. The rotary handle of claim 4 in which said second slide member comprises a projecting member slidable in a longitudinal slot defined by the other of said grip member and handle member.

6. The rotary handle of claim 4 in which said second slide member comprises a nut rotatably mounted about said thread and groove system, said nut being mounted to engage and to slide along a non-circular slide track of the other of said grip member and handle member, to permit said nut to slide longitudinally while preventing relative rotation between the nut and said other member.

7. The rotary handle of claim 2 in which said rotary slide member defines a coil spring.

8. The rotary handle of claim 7 in which said second slide member is positioned in fixed relation with said other member.

9. The rotary handle of claim 2 in which said one of said tubular grip member and handle member portion is the handle member portion.

10. The rotary handle of claim 9 in which said tubular grip member defined a bore that contains one end of said handle member portion, said bore also containing, distal to said handle member portion, an elastomeric retention block having a longitudinal passageway receiving a catheter proximal end, said passageway normally being of less diameter than the catheter end received therein, whereby said catheter is frictionally retained, to be rotatable with the tubular grip member.

11. The rotary handle of claim 10 in which the proximal end of the catheter defines a rigid, tubular tip, said catheter extending completely through said elastomeric retention block, said handle member portion defining a longitudinal bore extending through O-ring sealing means, said rigid, tubular tip extending through and engaging said O-ring means in sealing relation.

12. The rotary handle of claim 1 in which the distal end thereof defines a luer connector for receiving and holding a luer connector of a catheter end.

13. A rotary handle for attachment to a proximal end of a catheter, which comprises: a handle member; a tubular grip member rotatably affixed in generally coaxial relation about a portion of said handle member; means carried by the grip member for frictionally retaining and holding a catheter; said handle member and grip member together defining means permitting their relative rotation, and corresponding rotation of a connected catheter through a predetermined rotational range; said handle member carrying a helical slide member facing said grip member; a second slide member, rotatable with said grip member, said second slide member being positioned to rotationally slide between coils of said helical slide member as the grip member and handle member relatively rotate; means, associated with said helical slide member, limiting the range of said rotational sliding of said second slide member; said handle member defining a longitudinal bore, plus means for connecting said bore at one end thereof to a catheter proximal end; and connector hub means communicating with said bore at the other end thereof.

14. The rotary handle of claim 13 in which said tubular grip member defines a bore that contains one end of said handle member, said bore also containing, distal to said handle member, an elastomeric retention block having a longitudinal passageway for receiving a catheter proximal end, said passageway normally being of less diameter than the catheter end received therein, whereby said catheter is frictionally retained to be rotatable with the tubular grip member.

15. The rotary handle of claim 14 in which the proximal end of the catheter defines a rigid, tubular tip, said catheter extending completely through said elastomeric retention block, said handle member portion defining a longitudinal bore extending through O-ring sealing means, said rigid, tubular tip extending through said engaging O-ring means in sealing relation.

16. The rotary handle of claim 15 in which said helical slide member defines a thread and groove system.

17. A rotary handle for attachment to the proximal end of a catheter, which comprises: a handle member; a tubular grip member rotatably affixed in generally coaxial relation about a portion of said handle member; means carried by one of said handle member and grip member for connection to the proximal end of a catheter; said handle member and grip member together defining means permitting their relative rotation and corresponding rotation of a connected catheter; said handle member defining a longitudinal bore, plus means for connecting said bore at one end thereof to a catheter proximal end, and connector hub means communicating with said bore on the other end thereof; said tubular grip member defining a bore that contains one end of said handle member, one of the bores of said handle member and said tubular grip member containing, distal to the other of said bores, an elastomeric retention block having a longitudinal passageway for receiving a catheter proximal end, said passageway normally being of less diameter than the catheter end received therein whereby said catheter is frictionally retained, to be rotatable with the tubular grip member, said bores being generally continuous with each other.

18. The rotary handle of claim 17 in which a catheter is frictionally retained in said handle, the retained end of said catheter defining a rigid, tubular tip, said catheter end extending completely through said elastomeric retention block, the other of said bores extending through O-ring sealing means, said rigid, tubular tip extending through and engaging said O-ring means in sealing relation.

19. The rotary handle of claim 18 in which said elastomeric retention block is carried in the bore of said tubular grip member.

20. A rotary handle for attachment to the proximal end of a catheter, which comprises:
a handle member; a tubular grip member rotatably affixed in generally coaxial relation about a portion of said handle member; means carried by one of said handle member and grip member for connection to the proximal end of a catheter, one of said tubular grip member and handle member defining a bore which carries an elastomeric retention block having a longitudinal passageway for receiving a catheter proximal end, one of said elastomeric retention block and bore being of generally cylindrical periphery to snugly fit said retention block in the bore the other of said bore and retention block being shaped to form a plurality of space between the periphery of the retention block and the cylindrical bore, whereby said elastomeric retention block is capable of receiving a larger range of catheter diameters within the longitudinal passageway in firm retention therewith.

21. The rotary handle of claim 20 in which means are provided to permit said handle member and grip member to rotate through a predetermined rotational range, but to prevent further relative rotation and rotation of a catheter carried therein, to prevent over rotation of a catheter connected thereto while implaced in a patient.

22. The rotary handle of claim 20 in which said bore is cylindrical and said elastomeric retention lock is of generally cylindrical periphery except for a plurality of flattened areas defined in the periphery of the elastomeric retention block.

* * * * *